United States Patent
Whateley

(10) Patent No.: US 7,125,682 B2
(45) Date of Patent: Oct. 24, 2006

(54) METHODS FOR MEASURING PROTEIN KINASE AND PHOSPHATASE ACTIVITY

(75) Inventor: John G. Whateley, Cardiff (GB)

(73) Assignee: GE Healthcare UK Limited, Amersham (GB)

( * ) Notice: Subject to any disclaimer, the term of this patent is extended or adjusted under 35 U.S.C. 154(b) by 546 days.

(21) Appl. No.: 10/417,545

(22) Filed: Apr. 17, 2003

(65) Prior Publication Data

US 2003/0228646 A1 Dec. 11, 2003

(30) Foreign Application Priority Data

Apr. 19, 2002 (GB) .................................. 0208987.8

(51) Int. Cl.
*C12Q 1/48* (2006.01)
(52) U.S. Cl. ........................ 435/15; 435/21; 435/194
(58) Field of Classification Search ................ 435/15, 435/21, 194
See application file for complete search history.

(56) References Cited

U.S. PATENT DOCUMENTS

| | | | | |
|---|---|---|---|---|
| 5,032,381 A * | 7/1991 | Bronstein et al. | ............... | 435/4 |
| 5,981,200 A * | 11/1999 | Tsien et al. | ............... | 435/7.4 |
| 6,203,994 B1 * | 3/2001 | Epps et al. | ............... | 435/7.1 |
| 6,630,311 B1 * | 10/2003 | Epps et al. | ............... | 435/7.1 |
| 6,818,413 B1 * | 11/2004 | Epps et al. | ............... | 435/7.4 |

FOREIGN PATENT DOCUMENTS

| | | |
|---|---|---|
| EP | 1 264 897 | 12/2002 |
| JP | 11012297 | 1/1999 |
| JP | 2001019700 | 7/2001 |
| WO | WO 98/02571 | 1/1998 |
| WO | WO 99/29894 A1 * | 6/1999 |
| WO | WO 01/09372 | 2/2001 |

OTHER PUBLICATIONS

McIlroy, B. et al. A Continuous Fluorescence Assay for Protein Kinase C. Anal Biochemistry 195(1)148-152, 1991.*
McIlroy, B., et al., "A Continuous Fluorescence Assay for Protein Kinase C", *Analytical Biochemistry*, vol. 195, No. 1, 1991, p. 148-152.
Ohuchi, Y., et al., "A fluorescent-labeled oligopeptide for monitoring PKA-mediated phosphorylation", *The Analyst Communication*, vol. 125, 2000, p. 1905-1907.
Yeh, R., et al., "Real Time Visualization of Protein Kinase Activity in Living Cells", *The Journal of Biological Chemistry*, vol. 2777, No. 13, 2002, p. 11527-11532.

* cited by examiner

*Primary Examiner*—Ralph Gitomer
(74) *Attorney, Agent, or Firm*—Yonggang Ji

(57) ABSTRACT

The invention provides fluorescence-based assays for determining the phosphorylating or the dephosphorylating activity of an enzyme acting on a substrate molecule. The substrate comprises at least one moiety that is capable of being phosphorylated or dephosphorylated by an enzyme to yield a product, the substrate being labelled with a fluorescent dye, and which is capable of exhibiting change in fluorescence intensity and fluorescence lifetime upon phosphorylation of the dye-labelled substrate or upon dephosphorylation of the dye-labelled phosphorylated substrate. In preferred embodiments, the substrate is labelled with a fluorescent dye selected from the acridone and the quinacridone classes of dyes. Also provided is a method is provided for screening for a test agent whose effect on the phosphorylating or dephosphorylating activity of an enzyme is to be determined.

28 Claims, 9 Drawing Sheets

METHODS FOR MEASURING PROTEIN KINASE AND PHOSPHATASE ACTIVITY

BACKGROUND OF INVENTION

The present invention relates to fluorescence-based assays for measuring protein kinase and phosphatase activity.

Phosphorylation and dephosphorylation of proteins, catalysed respectively by protein kinases and protein phosphatases, are key intracellular processes that regulate cellular functions in eukaryotic cells. The reversible phosphorylation of serine, threonine and tyrosine residues in proteins is a highly effective means for regulating the biological properties of proteins so as to modulate such diverse processes as metabolism, cell division, transcription and translation of genes, and signal transduction mechanisms in cells. For reviews, see Hunter, T., Cell, (1995), 80, 225–236; Karin, M., Curr. Opin. Cell Biol., (1991), 3, 467–473. Thus, protein phosphorylation and dephosphorylation are significant events in an organism's maintenance, adaptation, and susceptibility to disease. Dysfunction in protein phosphorylation and dephosphorylation processes can have serious consequences for cellular regulatory mechanisms and for this reason, protein kinases and phosphatases are suitable targets for the development of high throughput screening assays of importance in the development of new therapeutic drug treatments.

Conventional assays for the detection and measurement of kinase activity include those based on radioactive detection methods using [$^{32}$P]- or [$^{33}$P]- labelled ATP as a phosphate source for incorporation of phosphate into a target substrate. Methods employing radioactive isotopes typically rely on a separation step to isolate the labelled product, prior to counting in a scintillation counter (Songyang, Z. et al, Nature, (1995), 373, 536–539).

Alternatively, assays involving non-radioactive detection have been employed, for example utilising antibodies to detect phosphorylated proteins and peptides. Detection modalities include fluorescence polarisation and time resolved fluorescence resonance energy transfer.

WO 99/29894 (Epps et al) relates to high throughput screening assays for protein kinases and phosphatases employing fluorescence detection. The methods utilize a competitive immunoassay procedure to determine the amount of substrate that is phosphorylated (or dephosphorylated) by the enzyme. Determination of enzyme activity is achieved by measuring fluorescence polarisation of a labelled antibody-product conjugate. Alternatively, fluorescence quenching or fluorescence correlation spectroscopy may be used.

WO 00/75167 (Sportsman et al) relates to methods for detecting the addition or removal of a phosphate group to or from a substrate by contacting a luminescent peptide with a binding partner that specifically binds to a phosphorylated peptide.

An alternative fluorescent assay method for protein kinase C (PKC) without antibody selection has been reported by Il et al (Analytical Biochemistry, (1991), 195, 148–152). In this assay, an acrylodan-labelled 25-amino acid synthetic peptide incorporating a PKC phosphorylation site is reported to undergo a 20% fluorescence decrease upon phosphorylation. The assay allows detection of PKC to a level of 0.2 nM, while similar concentrations of cyclic AMP-dependent or type II calmodulin dependent protein kinases produced no change in peptide fluorescence. JP 2001–19700-A discloses the use of a fluorogenic substrate for detecting cAMP dependent protein kinase A activity or protein dephosphorylation activity by measuring changes in fluorescence intensity.

In those assays that employ time resolved fluorescence resonance energy transfer (TR-FRET), more than one detection reagent is required. The preparation and addition of such reagents often requires considerable time, effort and expense. Many of the assays are not truly homogeneous in that they require addition of reagents after the reaction has been initiated. The dependence of TR-FRET on the distance between the detection reagents means that substrates must be engineered to meet that need. Furthermore, many of the assays will require multiple labels. It is not possible in most cases to use the natural substrate, even if desired, because the need to biotinylate proteins and add antibodies precludes their use.

SUMMARY OF INVENTION

Thus, there is a requirement in the art for novel, convenient, rapid and sensitive methods for the determination of kinase and phosphatase activities that are simple to perform, can be carried out with little technical intervention and are fully amenable to robotic automation.

In a first aspect there is provided a method for determining the phosphorylating activity of an enzyme acting on a substrate molecule, said substrate comprising at least one moiety that is capable of being phosphorylated by said enzyme to yield a phosphorylated product and wherein said substrate is labelled with a fluorescent dye, said method comprising the steps of:

i) measuring the fluorescence intensity and the fluorescence lifetime of the fluorescently labelled substrate;

ii) combining said enzyme with said substrate molecule in the presence of a phosphate donor; and iii) measuring a change in fluorescence intensity and in fluorescence lifetime of the fluorescent label following the combination of step ii);

wherein said change in fluorescence intensity and in fluorescence lifetime of the fluorescent label is used to determine the phosphorylating activity of said enzyme.

Preferably, the substrate is labelled with a fluorescent dye selected from the acridone and the quinacridone classes of dyes.

In a second aspect of the present invention, there is provided a method for determining the phosphorylating activity of an enzyme acting on a substrate molecule, said substrate comprising at least one moiety that is capable of being phosphorylated by said enzyme to yield a phosphorylated product and wherein said substrate is labelled with a fluorescent dye selected from the acridone and the quinacridone classes of dyes, said method comprising the steps of:

i) measuring the fluorescence intensity of the fluorescently labelled substrate;

ii) combining said enzyme with said substrate molecule in the presence of a phosphate donor; and iii) measuring an increase in fluorescence intensity of the fluorescent label following the combination of step ii);

wherein said increase in fluorescence intensity of the fluorescent label is used to determine the phosphorylating activity of said enzyme.

Suitably, according to the first and second aspects, the substrate molecule may be selected from natural proteins, (including post-translationally modified proteins such as glyco-proteins and lipo-proteins); and synthetic peptides. In these embodiments, the substrate molecule comprises at least one amino acid that is capable of being phosphorylated.

Alternatively, the substrate may be selected from a lipid, such as an inositol lipid including phosphatidyl mono- or bis-phosphate; or may be a mono- or poly-saccharide, in which case, the substrate molecule comprises at least one hydroxyl group that is capable of being phosphorylated.

In preferred embodiments, the substrate is a protein or a peptide and the amino acid that is capable of being phosphorylated is selected from tyrosine, serine, threonine and histidine. In these embodiments, the substrate is capable of being phosphorylated by a protein kinase, for example, one or more of the enzymes selected from tyrosine kinase, serine/threonine kinase and histidine kinase.

In an embodiment according to the second aspect wherein the substrate is phosphorylated at a tyrosine residue by a tyrosine kinase, the phosphorylated product comprises at least one phospho-tyrosine residue. In this embodiment, the measuring steps i) and iii) may additionally comprise measurement of the fluorescence lifetimes of the fluorescent label wherein an increase in fluorescence lifetime is used to measure the concentration of phosphorylated product relative to the concentration of non-phosphorylated substrate. Thus, the method may be used for continuous recording in real time, of the amount of substrate that is converted during the course of the enzymatic reaction and the corresponding increase in the amount of phosphorylated product produced thereby.

In another embodiment, the substrate is phosphorylated at a residue selected from serine, threonine and histidine.

BRIEF DESCRIPTION OF THE DRAWINGS

The present invention is further illustrated with reference to the following Figures and Examples in which.

DETAILED DESCRIPTION OF INVENTION

Figure 1:
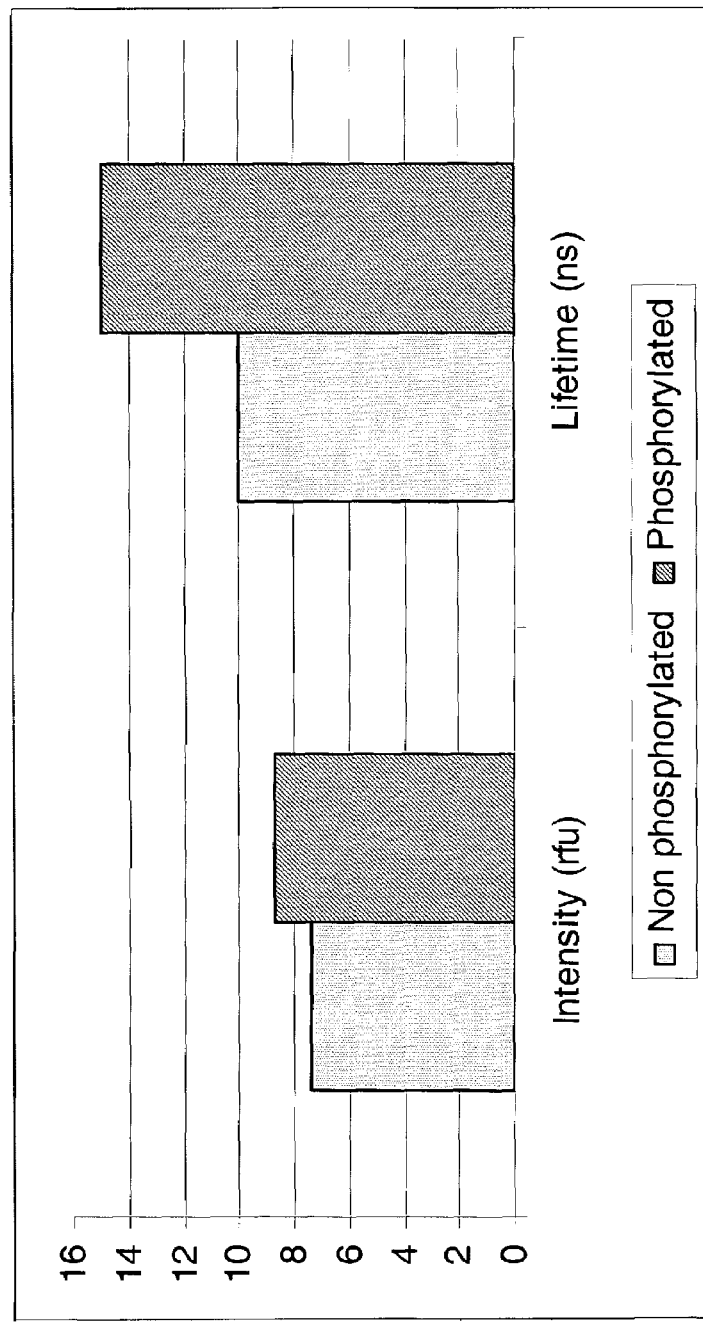
FIG. 1 illustrates the differences in lifetimes and intensities observed upon phosphorylation of Abl peptide according to Example 5.

In preferred embodiments according to the first or second aspects, there is provided a method of screening for a test agent whose effect on the phosphorylating activity of an enzyme is to be determined. The method comprises the steps of: (a) performing the method according to the first or second aspects in the presence and in the absence of said agent; and (b) determining the phosphorylating activity of the enzyme in the presence and in the absence of said agent; wherein a difference between the phosphorylating activity of said enzyme in the presence and in the absence of said agent is indicative of the effect of said test agent on the phosphorylating activity of said enzyme. Alternatively, the screening can be done by performing the method in the presence of a test agent and comparing the value of the phosphorylating activity of the enzyme with a control value for the enzyme activity in the absence of the test agent. The control value may conveniently be stored electronically in a database or other electronic format.

The term "phosphate donor" is intended to mean high energy phosphate donors such as ATP and GTP.

In a third aspect, there is provided a method for determining the dephosphorylating activity of an enzyme acting on a substrate molecule, said substrate comprising at least one phosphorylated moiety that is capable of being dephosphorylated by said enzyme to yield a product and wherein said substrate is labelled with a fluorescent dye, said method comprising the steps of:

i) measuring the fluorescence intensity and the fluorescence lifetime of the fluorescently labelled substrate;

ii) combining said enzyme with said substrate molecule to yield a product; and iii) measuring a change in fluorescence intensity and in fluorescence lifetime following the combination of step ii);

wherein said change in fluorescence intensity and in fluorescence lifetime of the fluorescent label is used to determine the dephosphorylating activity of said enzyme.

Preferably, the substrate is labelled with a fluorescent dye selected from the acridone and the quinacridone classes of dyes.

In a fourth aspect of the present invention, there is provided a method for determining the dephosphorylating activity of an enzyme acting on a substrate molecule, said substrate comprising at least one phosphorylated moiety that is capable of being de-phosphorylated by said enzyme to yield a product and wherein said substrate is labelled with a fluorescent dye selected from the acridone and the quinacridone classes of dyes, said method comprising the steps of:

i) measuring the fluorescence intensity of the fluorescently labelled substrate;

ii) combining said enzyme with said substrate molecule to yield a product; and iii) measuring a decrease in fluorescence intensity following the combination of step ii);

wherein said decrease in fluorescence intensity of the fluorescent label is used to determine the dephosphorylating activity of said enzyme.

Suitably, the enzyme according to the third and fourth aspects is a phosphatase.

Suitably, according to the third and fourth aspects, the substrate molecule may be selected from natural proteins, (including post-translationally modified proteins such as glyco-proteins and lipo-proteins); and synthetic peptides. In these embodiments, the substrate molecule comprises at least one phosphorylated amino acid that is capable of being dephosphorylated.

Alternatively, the substrate may be selected from a phospho-lipid (such as a phospho-inositide), or may be a phosphorylated derivative of a mono- or poly-saccharide. In this embodiment, the substrate molecule comprises at least one phosphorylated hydroxyl group that is capable of being dephosphorylated.

In preferred embodiments, the substrate is a phosphorylated protein or a phosphorylated peptide and the phosphorylated amino acid that is dephosphorylated may be selected from phospho-tyrosine, phospho-serine, phospho-threonine and phospho-histidine and a phosphatase enzymatically removes a phosphate group from said phosphorylated amino acid.

In a particular embodiment of the fourth aspect, the substrate comprises a phosphorylated tyrosine residue and the enzyme removes a phosphate group from a phosphotyrosine residue in the substrate. In this embodiment, the measuring steps i) and iii) may additionally comprise measurement of the fluorescence lifetimes of the fluorescent label wherein a decrease in fluorescence lifetime is used to measure the concentration of phosphorylated substrate relative to the concentration of product. Thus, the method may be used for continuous recording in real time, of the amount of phosphorylated substrate that is converted during the course of the enzymatic reaction and the corresponding increase in the amount of product produced thereby.

In preferred embodiments, there is provided a method of screening for a test agent whose effect on the dephosphorylating activity of an enzyme is to be determined. The method comprises the steps of: (a) performing the method according to the third or fourth aspects in the presence and in the absence of said agent; and (b) determining the dephosphorylating activity of said enzyme in the presence and in the absence of said agent; wherein a difference between the dephosphorylating activity of said enzyme in the presence and in the absence of said agent is indicative of the effect of said test agent on the dephosphorylating activity of said enzyme. Alternatively, the screening can be done by performing the method in the presence of a test agent and comparing the value of the dephosphorylating activity of the enzyme with a control value for the enzyme activity in the absence of the test agent. The control value may be conveniently stored electronically in a database or other electronic format.

In embodiments according to the invention, the kinase or the phosphatase substrate may be linked by a linker group to a solid support. In these embodiments, assays for determining the phosphorylating or the dephosphorylating activity of an enzyme may be performed in the solid phase.

In other embodiments, the kinase or the phosphatase substrate may be conjugated (or fused) to a second peptide or protein, such as a carrier or transport peptide as described in U.S. Pat. No. 5,807,746; WO 99/64455; WO 97/12912; WO 99/05302. See also, Rojas et al, Nature Biotechnology, (1998), 16, 370–375; Hawiger et al, Curr. Opinion Chem. Biol., (1999), 89–94). In such embodiments, the carrier peptide may be employed to transport the kinase or phosphatase substrate across a cellular membrane and into a cell so as to enable the study of the phosphorylation status of a substrate in a cellular environment.

Where the activity of a kinase is to be determined, the choice of a natural protein kinase substrate will depend upon the particular kinase to be assayed. Substrate specificity of protein kinases varies considerably and it is known that the local sequence adjacent to the phosphorylation site plays a critical role in the recognition of the substrate by protein kinases. Thus, the selection of a particular substrate for a kinase assay will depend on the phosphorylation site motifs present in the sequence. Table 1 lists some known protein kinase substrates and corresponding kinases that are suitable for use in the assay according to the invention.

TABLE 1

Protein Kinase Substrates

| Kinase | Protein Kinase Substrate |
|---|---|
| cAMP dependent protein kinase | Pyruvate kinase |
|  | Phosphorylase kinase |
|  | Histone H1 |
| Casein kinase I | Glycogen synthase |
|  | α-Casein |
| Casein kinase II | PKA regulatory subunit |
|  | $p34^{cdc2}$ |
|  | Acetyl co-enzyme A carboxylase |
| Protein kinase C | EGF receptor |
|  | Fibrinogen |
|  | Glycogen synthase |
|  | Myelin basic protein |
| cGMP dependent protein kinase | Histone |
|  | Phosphorylase kinase |
| Phosphorylase kinase | Phosphorylase |
| V-Abl | $pp60^{src}$ |
| AMP-activated protein kinase | Acetyl Co-enzyme A carboxylase |
| Glycogen synthase | Glycogen synthase kinase |

Advances in knowledge relating to kinase substrate specificity has made it possible to identify potential enzyme recognition sites in newly sequenced proteins, as well as to construct synthetic peptide model substrates. For reviews in this field, see Kennelly, P. J. and Krebs, E. G., J. Biol. Chem., (1991), 266, 15555–58; Kemp, B. E. and Pearson, R. B., Trends in Biochemical Sciences, (1990), 343. Suitable synthetic peptide substrates may be prepared by methods that are well known to the skilled person, for example by means of solid phase peptide synthesis methods by the sequential addition of protected amino acids linked (optionally through a linker group) to a solid phase support, as described in "Solid Phase Peptide Synthesis", Atherton, E. and Sheppard, R. C., IRL Press (1989).

Phosphatases in vitro generally display broad substrate specificity (unlike kinases), see Helps, N. R. et al, Biochem. J., (2000), 349, 509–518; Majeti, R. and Weiss, A., Chem. Rev. (2001), 101, 2441–2448; Cohen, P., J. Cell Science, (2002), 115, 241–256. In vivo, the phosphatase catalytic domain is associated with and targeted by a regulatory subunit. This combination means that phosphatase substrate specificity in vivo may be very specific. However, in in vitro assays, only the catalytic domain is assayed. Consequently, phosphatases in vitro are able to act on a wide range of both peptide and protein substrates.

The substrate used in kinase and phosphatase assays according to the invention is labelled with a fluorescent dye that is capable of exhibiting a change in fluorescence intensity and in fluorescence lifetime upon phosphorylation of the dye-labelled substrate, or upon dephosphorylation of a dye-labelled phosphorylated substrate. Thus, there may be an increase in fluorescence intensity and in fluorescence lifetime upon phosphorylation of the dye-labelled substrate. Alternatively, there may be a decrease in fluorescence intensity and in fluorescence lifetime upon dephosphorylation of the dye-labelled phosphorylated substrate. Dyes suitable for use in the present invention are fluorescence lifetime dyes. In the context of the present invention, the term "lifetime dye" is intended to mean a dye having a measurable fluorescence lifetime, defined as the average amount of time that the dye remains in its excited state following excitation (Lackowicz, J. R., Principles of Fluorescence Spectroscopy, Kluwer Academic/Plenum Publishers, New York, (1999)). Suitably, the fluorescent dye may be selected from the acridone and the quinacridone classes of dyes. Acridone and quinacridone derivatives for use as labels for fluorescence detection of target materials are described in, respectively, WO 02/099424 A2 and WO 02/099432 A2.

Acridone dyes suitable for use in the method of the invention are those having the general formula (I):

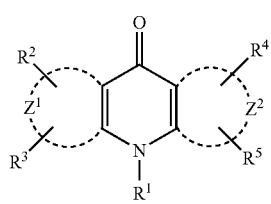

(I)

wherein:
groups $R^2$ and $R^3$ are attached to the $Z^1$ ring structure and groups $R^4$ and $R^5$ are attached to the $Z^2$ ring structure;
$Z^1$ and $Z^2$ independently represent the atoms necessary to complete one or two fused ring aromatic or heteroaromatic systems, each ring having five or six atoms selected from carbon atoms and optionally no more than two atoms selected from oxygen, nitrogen and sulphur;
$R^1$, $R^2$, $R^3$, $R^4$ and $R^5$ are independently selected from hydrogen, halogen, amide, hydroxyl, cyano, amino, mono- or di-$C_1$–$C_4$ alkyl-substituted amino, sulphydryl, carbonyl, $C_1$–$C_6$ alkoxy, aryl, heteroaryl, $C_1$–$C_{20}$ alkyl, aralkyl; the group -E-F where E is a spacer group having a chain from 1–60 atoms selected from the group consisting of carbon, nitrogen, oxygen, sulphur and phosphorus atoms and F is a target bonding group; and the group —(CH$_2$—)$_n$Y where Y is selected from sulphonate, sulphate, phosphonate, phosphate, quaternary ammonium and carboxyl and n is zero or an integer from 1 to 6.

Quinacridone dyes suitable for use in the method of the invention are those having the general formula (II):

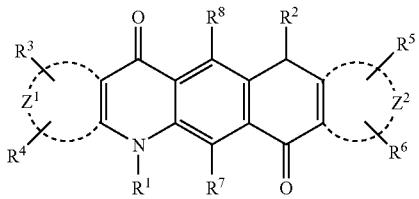

(II)

wherein:
groups $R^3$ and $R^4$ are attached to the $Z^1$ ring structure and groups $R^5$ and $R^6$ are attached to the $Z^2$ ring structure;
$Z^1$ and $Z^2$ independently represent the atoms necessary to complete one or two fused ring aromatic or heteroaromatic systems, each ring having five or six atoms selected from carbon atoms and optionally no more than two atoms selected from oxygen, nitrogen and sulphur;
$R^1$, $R^2$, $R^3$, $R^4$, $R^5$, $R^6$, $R^7$ and $R^8$ are independently selected from hydrogen, halogen, amide, hydroxyl, cyano, amino, mono- or di-$C_1$–$C_4$ alkyl-substituted amino, sulphydryl, carbonyl, carboxyl, $C_1$–$C_6$ alkoxy, aryl, heteroaryl, $C_1$–$C_{20}$ alkyl, aralkyl; the group -E-F where E is a spacer group having a chain from 1–60 atoms selected from the group consisting of carbon, nitrogen, oxygen, sulphur and phosphorus atoms and F is a target bonding group; and the group —(CH$_2$—)$_n$Y where Y is selected from sulphonate, sulphate, phosphonate, phosphate, quaternary ammonium and carboxyl and n is zero or an integer from 1 to 6.

Suitably, the target bonding group F is a reactive or functional group. A reactive group of the fluorescent dyes according to formula (I) and formula (II) can react under suitable conditions with a functional group of the substrate; a functional group of a compound according to formula (I) and formula (II) can react under suitable conditions with a reactive group of the substrate. By virtue of these reactive and functional groups, the fluorescent dyes according to formula (I) and formula (II) may be reacted with and covalently bond to the substrate, such that the substrate becomes labelled with the fluorescent dye.

Preferably, when F is a reactive group, it is selected from succinimidyl ester, sulpho-succinimidyl ester, isothiocyanate, maleimide, haloacetamide, acid halide, vinylsulphone, dichlorotriazine, carbodiimide, hydrazide and phosphoramidite. Preferably, when F is a functional group, it is selected from hydroxy, amino, sulphydryl, imidazole, carbonyl including aldehyde and ketone, phosphate and thiophosphate.

Preferred examples of acridone and quinacridone dyes (and their corresponding lifetimes (nsecs)) are shown as compounds (III), (IV), (V), (VI) and (VII) in Table 2.

TABLE 2

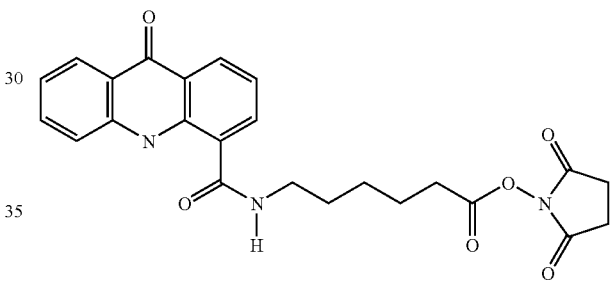

(III) (4nsec)
O-(N-Succinimidyl)-6-(9-oxo-9H-acridin-4-carboxamido)hexanoate (III)

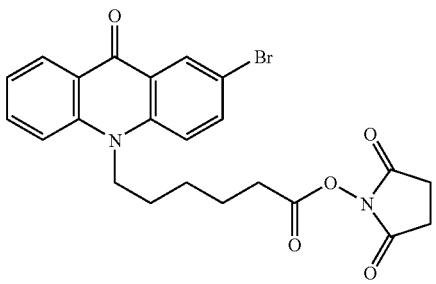

(IV) (8nsec)
O-(N-Succinimidyl)-6-(2-bromo-9-oxo-9H-acridin-10-yl)hexanoate (IV)

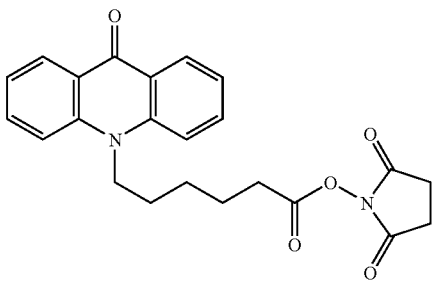

(V) (14nsec)

TABLE 2-continued

O-(N-Succinimidyl)-6-(9-oxo-9H-acridin-10-yl)hexanoate (V)

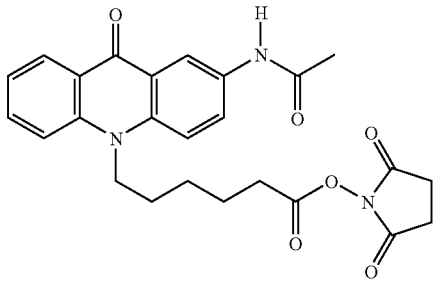

(VI) (17nsec)
O-(N-Succinimidyl)-6-(2-acetamido-9-oxo-9H-acridin-10-yl)hexanoate (VI)

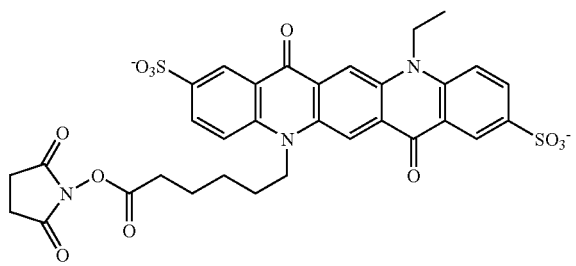

(VII) (22nsec)
O-(N-Succinimidyl)-6-(12-ethyl-7,14-dioxo-2,9-disulpho-7,14-dihydroquino[2,3-b]acridin-5(12H)-yl)hexanoate (VII)

The dye-labelled protein and peptide substrate may be prepared by direct chemical coupling of a reactive fluorescent dye derivative to the protein or peptide by techniques that are well known to the skilled person. An alternative labelling strategy may involve coupling (or ligating) the substrate to a polypeptide label, such as a fluorescent polypeptide. Peptide and protein substrates for use in the invention may be labelled at a terminal amino acid position, or alternatively at one or more internal amino acid positions.

The chemistry of labelling protein and peptides with fluorescent dyes is well documented and a variety of chemistries is available for the chemical modification of peptides. Generally, the choice of labelling reagent will be determined by the amino acid composition of the protein or peptide to be labelled. Particularly preferred are amine-reactive and thiol-reactive fluorescent labelling dyes. In the first case, the functional group for labelling is a primary amino group, which may be derived from the ε-amino group of lysine, or alternatively the amino-terminus of the peptide or protein. Particular examples of reactive groups for labelling ε-amino lysine residues include the isothiocyanato- and N-hydroxysuccinimidyl (NHS) ester derivatives of a fluorescent dye. Although relatively few proteins and peptides have free thiol groups (they generally exist as disulphide groups), thiol labelling procedures have proved very useful for labelling proteins and peptides, using thiol-reactive reagents, for example, iodoacetyl and maleimidyl derivatives of fluorescent dyes. For reviews and examples of protein labelling using fluorescent dye labelling reagents, see "Non-Radioactive Labelling, a Practical Introduction", Garman, A. J. Academic Press,1997; "Bioconjugation—Protein Coupling Techniques for the Biomedical Sciences", Aslam, M. and Dent, A., Macmillan Reference Ltd, (1998). Protocols are available to obtain site specific labelling in a synthesised peptide, for example, see Hermanson, G. T., Bioconjugate Techniques, Academic Press (1996). In a typical example, N-hydroxy-succinimidyl (NHS) esters of the acridone dyes, may be linked to polypeptides in a weak carbonate buffer at pH 9. The reaction is allowed to proceed for a suitable time, typically in the range 30 to 60 minutes. Unreacted or free dye may be removed by gel exclusion chromatography or by dialysis. Site specific fluorescent dye labelling of the substrate may be obtained during synthesis of the peptide, either by the use of a labelled amino acid in the synthesis process, or by the specific deprotection and labelling of the residue of interest before deprotection of other potentially reactive residues at the completion of the synthesis.

The assay methods according to the present invention are suitably performed in the wells of a multiwell plate, e.g. a microtitre plate having 24, 96, 384 or higher densities of wells, e.g. 1536 wells. Alternatively, the assays may be conducted in assay tubes or in the microchannels of a microfluidic device. In a typical kinase assay according to the first aspect, a kinase is contacted with a substrate molecule in the presence of a high-energy phosphate donor such as ATP or GTP. The reaction may be performed with the substrate and phosphate donor initially present in an aqueous assay buffer, suitably, 10 mM MOPs, 50 mM Tris or 50 mM HEPES, containing 5 mM $MgCl_2$. The assay may be performed either in the presence of, or the absence of a sample of a test agent. Suitably, the components of the reaction mixture, minus the initiator, are pre-dispensed into the wells of a microtitre plate. The reaction is then initiated by the addition of the enzyme. Alternatively, a reaction mixture may be prepared containing enzyme and substrate in a suitable buffered solution. In this case, the reaction is initiated by the addition of the phosphate donor.

Typically, kinase assays are performed under "stopped" conditions. Thus, the reaction is allowed to proceed for a predetermined time and then the reaction is terminated with a stop reagent, normally an inhibitor of the enzyme activity, which is often non-specific. An example of a stop reagent is EDTA, which is used to sequester metal ions that are normally required for enzymatic activity.

Measurements of fluorescence intensity and fluorescence lifetime may be made using instruments incorporating photo-multiplier tubes as detectors. Typically, methods for the measurement of fluorescence lifetime may be based on: i) time correlated single photon counting, or ii) frequency domain (as described in Principles of Fluorescence Spectroscopy by J R Lakowicz, $2^{nd}$ Ed, 1999, Chapters 4 and 5 Kluwer/Academic Press, New York), or on time gating (see for example, Sanders, et al, Analytical Biochemistry, (1995), 227(2), 302–308). Changes in fluorescence intensity may be measured by means of a charge coupled device (CCD) imager (such as a scanning imager or an area imager) to image all of the wells of a microtitre plate. The LEADseeker™ system features a CCD camera allowing fluorescence imaging of high density microtitre plates in a single pass. Imaging is quantitative and fast, and instrumentation suitable for imaging applications can now simultaneously image the whole of a multiwell plate.

Where an assay is to be formatted for the determination of the activity of a test agent on kinase activity, the assay may be performed under continuous measurement of the fluorescence of the substrate. In this format, the intensity of the fluorescent labelled substrate changes continuously. The labelled substrate does not need separation from the product of the enzymatic reaction and thus, a time-course of the reaction may be obtained, allowing kinetic studies to be performed in real time.

In a particular embodiment of the first or second aspects, the enzyme is a tyrosine kinase and the substrate is a peptide substrate specific for that enzyme, such as Abl peptide. The assay may be performed in a microtitre plate in aqueous conditions, using either HEPES, Tris or MOPs buffer at a pH of 7–8. Typically, the buffer concentration will be about 50 mM. Depending on the enzyme whose activity is to be measured, salts such as sodium or potassium chloride may be added. The preferred phosphate donor is ATP, which is typically present at a concentration of $2 \times K_m$, i.e. in the range 30–200 µM. The enzyme substrate should be present at an optimal concentration of at or below $K_m$, which will typically be in the range 1–100 µM. Additional cofactors, such as $Mg^{2+}$ ions may also be present at a suitable concentration for the given enzyme, typically in the range of 1–10 mM.

The substrate is labelled with a dye chosen from the acridone class of dyes, preferably O-(N-succinimidyl)-6-(9-oxo-9H-acridin-10yl) hexanoate. The non-phosphorylated peptide substrate may be distinguished from the phosphorylated form of the substrate by detecting and measuring differences between the lifetime of the dye attached to the non-phosphorylated substrate and the lifetime of the dye attached to the phosphorylated substrate. Thus, changes, both in the intensity and the lifetime, can be monitored simultaneously, thereby allowing a dual parameter measurement of the assay. This gives a number of advantages. Firstly, the biology of the assays can be confirmed by the appearance of the lifetime, characteristic for the product of the enzymatic reaction and the intensity of the product can be simultaneously monitored. Secondly, the removal of the substrate can be monitored by its characteristic fluorescence lifetime and the fluorescence intensity of the dye-labelled substrate can be observed to decline. Thirdly, it will be possible to determine a quantitative relationship between the intensity of each species; this can be converted directly into concentration units for on-line, real-time monitoring of the reaction.

Where the activity of a phosphatase is to be determined, a phosphorylated substrate is first prepared. A peptide substrate may be synthesised and then phosphorylated, or alternatively, one or more phosphorylated amino acids may be incorporated into the peptide chain during synthesis. Phosphorylated amino acids suitable for incorporation into chemically synthesised peptides may be obtained commercially, for example from Bachem A.G. Fluorescent dye labelling of a phosphorylated peptide may be carried out as above during the synthesis of the peptide, either by the use of a labelled amino acid in the synthesis process, or by the specific deprotection and labelling of the residue of interest before deprotection of other potentially reactive residues at the completion of the synthesis. Protein phosphatase substrates must first be in, or converted into, a suitable phosphorylated form, for use in the assays according to the invention. For example, phosphorylase b (de-phosphorylated form) may be phosphorylated at a single serine residue using phosphorylase kinase to obtain phosphorylase a. The phosphorylated substrate is then labelled with a fluorescent dye labelling reagent, preferably, an acridone or a quinacridone.

Assay methods for phosphatases may be performed in an aqueous buffered medium, where the buffer is typically in the range 10–200 mM at pH 7–8, for example 50 mM Tris pH 7.2 (or alternatively, HEPES or MOPS). Additionally, salts such as sodium chloride may be added in the range 10–100 mM. Other factors such as DTT, 1–5 mM, EDTA, 100 µM–2 mM, and 0.05–0.1% Brij™ may also be included in the assay mix. The dye-labelled phosphorylated substrate is present in the range from 10–200 µM. Reactions are initiated by the addition of phosphatase. Generally reactions are incubated for 30–60 minutes at 30° C. and then stopped by addition of a stop reagent as before.

The methods according to the present invention may also be employed to measure the phosphorylation status of a kinase and phosphatase substrate present in a cellular environment by means of cell-based assays.

Thus, in a fifth aspect of the present invention there is provided a method for determining the phosphorylation status of a substrate in a cellular environment, the substrate comprising at least one moiety that is capable of being phosphorylated or dephosphorylated by a cellular enzyme to yield a product, and wherein said substrate is labelled with a fluorescent dye, said method comprising the steps of:

i) measuring the fluorescence intensity and the fluorescence lifetime of the fluorescently labelled substrate in a cell-free environment;

ii) adding the substrate to one or more cells in a fluid medium; and iii) measuring the fluorescence intensity and the fluorescence lifetime of the fluorescent label following step ii);

wherein a change in the fluorescent intensity and the fluorescence lifetime is used to indicate the phosphorylation status of said substrate.

Suitably, the substrate according to the fifth aspect is a kinase substrate or a phosphatase substrate.

Preferably, the fluorescent dye is selected from the acridone and the quinacridone classes of dyes as described hereinbefore.

Suitably, the substrate is conjugated (or fused) to a second peptide or protein, such as a carrier or transport peptide, which facilitates transport of the substrate across the cellular membrane and into the cell.

Typically, cultured cells are incubated with the conjugate at a concentration of 0.1 to 100 µM in a suitable cell culture medium under conditions suitable for cell growth and for a time that may range from 0.5 to 24 hours. Cells are cultured according to standard cell culture techniques, e.g. cells are cultured in a suitable vessel in a sterile environment at 37° C. in an incubator containing a humidified 95% air/5% $CO_2$ atmosphere. Vessels may contain stirred or stationary cultures. Various cell culture media may be used including media containing undefined biological fluids such as foetal calf serum, as well as media which is fully defined, such as 293 SFM II serum free media (Life Technologies Ltd., Paisley, UK). There are established protocols available for the culture of diverse cell types. (See for example, Freshney, R. I., Culture of Animal Cells: A Manual of Basic Technique, $2^{nd}$ Edition, Alan R.Liss Inc. 1987).

The method of the invention may be used with any adherent or non-adherent cell type that can be cultured in standard tissue culture plastic-ware. Such cell types include all normal and transformed cells derived from any recognised source, for example mammalian, plant, bacterial, viral or fungal, and with respect to species (e.g. human, rodent, simian), tissue source (e.g. brain, liver, lung, heart, kidney skin, muscle) and cell type (e.g. epithelial, endothelial). When the substrate is required to be delivered to cells grown in cell or tissue culture, the conjugate is simply added to the culture medium.

In a particular embodiment of the fifth aspect, the cells may be contacted with the conjugate in the presence of a substance whose effect on the phosphorylation status of the substrate is to be determined. In this embodiment, the detection step provides a measurement of the effect of the test substance on the phosphorylation status and may be applied to a compound whose metabolism and toxicology towards a particular cell type is under investigation, e.g. drugs, enzyme inhibitors, and the like.

The fluorescent dyes of each of the acridone and quinacridone classes of dyes may be distinguished one from the other by virtue of their different lifetimes. Thus, two or more different substrates, each one labelled with a different one of a set of acridone dyes (or with a different one of a set of quinacridone dyes) may be used in multiplex assays in which the measurement of the kinase activities of different enzymes may be performed simultaneously.

In a sixth aspect of the present invention, there is provided a method of simultaneously measuring the kinase activities of two or more different enzymes, each enzyme specific for a different substrate, wherein each substrate comprises at least one moiety that is capable of being phosphorylated by an enzyme to yield a product, and wherein each said substrate is labelled with a different one of a set of fluorescent dyes, said method comprising the steps of:
i) measuring the fluorescence intensity and the fluorescence lifetime of each of the fluorescently labelled substrates;
ii) combining a mixture of said enzymes with each of said substrate molecules in the presence of a phosphate source; and
iii) measuring an increase in fluorescence intensity and in fluorescence lifetime of each of the fluorescent labels following the combination of step ii);

wherein said increase in fluorescence intensity and in fluorescence lifetime of each of the fluorescent labels is used to determine the phosphorylating activity of each of said enzymes.

Preferably, the fluorescent dyes in said set are selected from the acridone and the quinacridone classes of dyes as described hereinbefore.

In one embodiment according to the sixth aspect, the method may be performed in vitro, either using isolated enzymes, or alternatively, one or more of said enzymes may be a component of a cell lysate.

In another embodiment according to the sixth aspect, the method may be performed in a cellular environment. In this embodiment, each of the different substrates is conjugated (or fused) to a second peptide or protein, such as a carrier or transport peptide, which facilitates transport of the substrate across the cellular membrane and into the cell as described.

Preferably, the measurement of kinase whose activity is being measured is a tyrosine kinase.

In a seventh aspect, there is provided a composition comprising:
i) a substrate for a kinase enzyme said substrate comprising at least one moiety that is capable of being of phosphorylated by said enzyme, to yield a phosphorylated product and wherein said substrate is labelled with a fluorescent dye selected from the acridone and the quinacridone classes of dyes; and
ii) a component selected from a phosphate donor and said kinase.

In a eighth aspect, there is provided a test kit for measuring the kinase activity of at least one enzyme, the test kit comprising:
i) one or more different substrates wherein each of said substrates comprises a moiety that is capable of being of phosphorylated to yield a product and wherein each of said substrates is labelled with different one of a set of fluorescent dyes selected from the acridone and the quinacridone classes of dyes; and optionally,
ii) one or more different enzymes each enzyme specific for a different substrate.

In a ninth aspect, there is provided a test kit for measuring the phosphatase activity of at least one enzyme, the test kit comprising:
i) one or more different substrates wherein each of said substrates comprises a phosphorylated moiety that is capable of being of dephosphorylated to yield a product and wherein each of said substrates is labelled with different one of a set of fluorescent dyes selected from the acridone and the quinacridone classes of dyes; and optionally,
ii) one or more different enzymes each enzyme specific for a different substrate.

The present invention simplifies conventional assay methodologies by reducing the number of steps required. Furthermore, in conventional (radioactive based) kinase assays, the concentration of the phosphate donor cannot be utilised at an optimal concentration. For example, in radioactive assays the ATP concentration can often be at 1/10 of $K_m$ (this will typically be 1–10 µM), whereas it is usually recommended to perform kinase assays at 2 fold or higher $K_m$ for ATP. In the present invention, the concentration of ATP does not affect the read-out and can therefore be utilised at optimal levels for the assay, independent of the fluorescent read-out technology.

According to the method of the present invention, it is possible to add any of the reagents to the mix in any order, while omitting a critical component. Thus, a reaction mixture may be prepared omitting ATP, but including all other components of the reaction. Prior to adding the ATP (initiator), the reaction can then be monitored for non-specific effects. It is also possible to construct mixture with no enzyme for further controls. Due to the nature of the reactions, it is then possible to add the final component and monitor changes either in real time or by stopping the reaction following the initiation step.

Furthermore, fluorescence lifetime measurements that may be utilised in the present invention can offer significant advantages over conventional fluorescence techniques that are based solely on quantifying fluorescence intensity. Fluorescence lifetime is determined from the same spectrally resolved intensity signal, but is additionally resolved in the temporal domain. Fluorescence lifetime techniques provide greater sensitivity because the signal is largely unaffected by 'background noise'. A further advantage with this technique is that several different events can be measured simultaneously by selecting labels having distinguishable lifetimes, thus enabling multiplexing. In addition, measurements of fluorescence lifetime are unaffected by concentration effects and photobleaching.

EXAMPLES

It will be readily apparent to those skilled in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

Example 1

Labelling of H-Glu-Ala-Ile-Tyr-Ala-Ala-Pro-Phe-Ala-Lys-Lys-Lys-NH₂ with O-(N-Succinimidyl)-6-(9-oxo-9H-acridin-10yl) hexanoate 1.1 H-Glu-Ala-Ile-Tyr-Ala-Ala-Pro-Phe-Ala-Lys-Lys-Lys-Rink Amide Resin; H-Glu-Ala-Ile-Tyr(PO₃H₂)-Ala-Ala-Pro-Phe-Ala-Lys-Lys-Lys-Rink Amide Resin H-Glu-Ala-Ile-Tyr-Ala-Ala-Pro-Phe-Ala-Lys-Lys-Lys-Rink Amide resin and H-Glu-Ala-Ile-Tyr(PO₃H₂)-Ala-Ala-Pro-Phe-Ala-Lys-Lys-Lys Rink Amide resin were synthesised using a commercially available Applied Biosystems Model 433A automated peptide synthesiser and FastMoc™ chemistry, following the instrument manufacturer's recommended procedures throughout. Both syntheses were performed on a 0.25 millimolar scale.

1.2 Synthesis of H-Glu-Ala-Ile-Tyr-Ala-Ala-Pro-Phe-Ala-Lys-Lys-Lys-NH₂ (Abl Kinase Substrate)

Crude peptide was deprotected and cleaved from the solid phase using a mixture of 95% trifluoroacetic acid:2.5% water:2.5% triisopropylsilane. The crude peptide obtained from the cleavage reaction was purified by conventional C-18 reverse phase HPLC using a linear gradient of water/acetonitrile (both containing 0.1% trifluoroacetic acid). After purification, the peptide was lyophilised and characterised by Maldi TOF mass spectroscopy and HPLC.

1.3 Synthesis of H-Glu-Ala-Ile-Tyr(PO₃H₂)-Ala-Ala-Pro-Phe-Ala-Lys-Lys-Lys-NH₂

This was prepared as in 1.2 above, using H-Glu-Ala-Ile-Tyr(PO₃H₂)-Ala-Ala-Pro-Phe-Ala-Lys-Lys-Lys Rink Amide Resin.

1.4 Labelling of H-Glu-Ala-Ile-Tyr-Ala-Ala-Pro-Phe-Ala-Lys-Lys-Lys-NH₂ with O-(N-Succinimidyl)-6-(9-oxo-9H-acridin-10yl) hexanoate (Ace-14)

H-Glu-Ala-Ile-Tyr-Ala-Ala-Pro-Phe-Ala-Lys-Lys-Lys-Rink Amide resin was labelled at the N-terminus on solid phase, with O-(N-succinimidyl)-6-(9-oxo-9H-acridin-10yl) hexanoate (1.5eq) (Amersham Biosciences) in dimethylsulphoxide and diisopropylethylamine (4% by volume), overnight at room temperature. The resin was washed with DMSO, followed by methanol and finally with dichloromethane and then dried in vacuo. The labelled peptide was deprotected and cleaved from the solid phase using a mixture of 95% trifluoroacetic acid:2.5% water:2.5% triisopropylsilane. The crude material isolated by precipitation from cold diethyl ether and purified by C-18 reverse phase HPLC using a linear gradient of water/acetonitrile (both containing 0.1% trifluoroacetic acid). After purification, the mono-labelled peptide was lyophilised and characterised by Maldi TOF mass spectroscopy, UV and HPLC.

1.5 Labelling of H-Glu-Ala-Ile-Tyr(PO₃H₂)-Ala-Ala-Pro-Phe-Ala-Lys-Lys-Lys-NH₂ with of O-(N-Succinimidyl)-6-(9-oxo-9H-acridin-10yl) hexanoate (Ace-14)

This was prepared as in 1.4 above, except that H-Glu-Ala-Ile-Tyr(PO₃H₂)-Ala-Ala-Pro-Phe-Ala-Lys-Lys-Lys Rink Amide resin was used.

Example 2

Labelling of Myelin Basic Protein (MBP) with O-(N-Succinimidyl)-6-(9-oxo-9H-acridin-10yl) hexanoate i) Method 1

100 mg of MBP (100 mg; 7 mg/ml) was dialysed overnight at +4° C. in 0.1 m NaHCO₃ solution. O-(N-Succinimidyl)-6-(9-oxo-9H-acridin-10yl) hexanoate (10 mg) was dissolved in 1 ml DMSO (Aldrich) and added to the sample of dialysed MBP. The resulting mixture was stirred for 45 minutes. 10 PD10 columns (Amersham Biosciences) were equilibrated with 10 ml of 10 mM MOPS pH 7.2. Labelled MBP (1.3 ml aliquots) was added to each column and the columns were washed with 10 mM MOPS (1 ml). Each column was eluted with 3 ml of 10 mM MOPS and the eluants pooled. The final protein concentration was determined using Biorad Protein Assay (500–006), with BSA as a standard (0.1 mg/ml). The final concentration of MBP was 1.44 mg/ml in a total volume of 30 ml. The labelled MBP was concentrated using Amicon Centripreps YM-10 (10,000 NMWL) (spun for 15 mins). Subsequent protein determination gave a concentration of 4.5 mg/ml (7.1 ml). The acridone labelled MBP was diluted with 500 mM MOPS pH 7.2, 50 mM MgCl₂, 1 mM ATP and PF H₂O to a concentration of 16.6 μM.

ii) Method 2

MBP (100 mg; 7 mg/ml) was dialysed overnight at +4° C. in a PBS solution (0.01M phosphate buffer, 0.0027 M potassium chloride and 0.137 M sodium chloride, pH 7.4) Sigma P-4417. O-(N-Succinimidyl)-6-(9-oxo-9H-acridin-10yl) hexanoate (10 mg) was dissolved in 1 ml DMSO (Aldrich) and added to the dialysed MBP. The mixture was roller-mixed overnight at +4° C. 10 PD10 columns (Amersham Biosciences) were equilibrated with 10 ml of 10 mM MOPS pH 7.2. Aliquots of 1.3 ml of labelled MBP were added to each column, each column was washed with a further 1 ml of 10 mM MOPS. Each column was then eluted with 3 ml of 10 mM MOPS and the eluants pooled. The protein concentration was determined using a Biorad Protein Assay (500–006) with BSA as a standard at 0.1 mg/ml. The concentration of the labelled MBP was found to be 1.4 mg/ml in a total volume of 28 ml. The labelled MBP was re-concentrated using Amicon Centripreps YM-10 (10,000 NMWL) (spun for 10 mins). Subsequent protein determination gave a concentration of 3.25 mg/ml in a total volume of 9.7 ml. The dye labelled MBP was diluted with 500 mM MOPS pH 7.2, 50 mM MgCl₂, 1 mM ATP and PF H₂O to a concentration of 16.6 μM.

Example 3

Labelling of H-Glu-Pro-Glu-Gly-Ile-Tyr-Gly-Val-Leu-Phe-NH₂ with O-(N-Succinimidyl)-6-(9-oxo-9H-acridin-10yl) hexanoate 3.1 H-Glu-Pro-Glu-Gly-Ile-Tyr-Gly-Val-Leu-Phe-Rink Amide Resin (Lck Kinase Substrate); H-Glu-Pro-Glu-Gly-Ile-Tyr(PO₃H₂)-Gly-Val-Leu-Phe-Rink Amide Resin H-Glu-Pro-Glu-Gly-Ile-Tyr-Gly-Val-Leu-Phe-Rink Amide resin and H-Glu-Pro-Glu-Gly-Ile-Tyr(PO₃H₂)-Gly-Val-Leu-Phe-Rink Amide resin were synthesised using a commercially available Applied Biosystems Model 433A automated peptide synthesiser and FastMoc™ chemistry, following the instrument manufacturer's recommended procedures throughout. The synthesises were performed on a 0.25 millimolar scale.

3.2 Labelling of H-Glu-Pro-Glu-Gly-Ile-Tyr-Gly-Val-Leu-Phe-NH$_2$ with O-(N-Succinimidyl)-6-(9-oxo-9H-acridin-10yl) hexanoate (Ace-14)

H-Glu-Pro-Glu-Gly-Ile-Tyr-Gly-Val-Leu-Phe-Rink Amide resin was labelled at the N-terminus on solid phase, with O-(N-succinimidyl)-6-(9-oxo-9H-acridin-10yl) hexanoate (1.5 eq) (Amersham Biosciences) in dimethylsulphoxide and diisopropylethylamine (4% by volume), overnight at room temperature. The resin was washed with DMSO, followed by methanol and finally with dichloromethane and then dried in vacuo. The labelled peptide was deprotected and cleaved from the solid phase using a mixture of 95% trifluoroacetic acid:2.5% water:2.5% triisopropylsilane. The crude material isolated by precipitation from cold diethyl ether and purified by C-18 reverse phase HPLC using a linear gradient of water/acetonitrile (both containing 0.1% trifluoroacetic acid). After purification, the mono-labelled peptide was lyophilised and characterised by Maidi TOF mass spectroscopy, UV and HPLC.

3.3 Labelling of H-Glu-Pro-Glu-Gly-Ile-Tyr(PO$_3$H$_2$)-Gly-Val-Leu-Phe-NH$_2$ with O-(N-Succinimidyl)-6-(9-oxo-9H-acridin-10yl) hexanoate (Ace-14)

This was prepared as in 3.2 above, except that H-Glu-Pro-Glu-Gly-Ile-Tyr(PO$_3$H$_2$)-Gly-Val-Leu-Phe-Rink Amide Resin was used.

3.4 Labelling of H-Glu-Pro-Glu-Gly-Ile-Tyr-Gly-Val-Leu-Phe-NH$_2$ with O-(N-Succinimidyl)-6-(2-acetamido-9-oxo-9H-acridin-10yl) hexanoate (Ace-17)

These syntheses were performed as described in Example 3.2, except that O-(N-succinimidyl)-6-(2-acetamido-9-oxo-9H-acridin-10yl) hexanoate (Ace-17) was used in place of O-(N-succinimidyl)-6-(9-oxo-9H-acridin-10yl) hexanoate (Ace-14).

Example 4

Labelling of H-Thr-Arg-Asp-Ile-Tyr(PO$_3$H$_2$)--Glu-Thr-Asp-NH$_2$ with O-(N-Succinimidyl)-6-(9-oxo-9H-acridin-10yl) hexanoate This synthesis was performed as described in Example 3.2, except that H-Thr-Arg-Asp-Ile-Tyr(PO$_3$H$_2$)-Glu-Thr-Asp-Rink amide resin was used. The non-phosphorylated peptide was synthesised in a similar way.

Example 5

Detection of Phosphorylated and Non-phosphorylated Peptides Using Abl Peptides

1 µM solutions of the phosphorylated and non-phosphorylated forms of the Abl peptide were prepared in 10 mM MOPs buffer pH 7.2. The fluorescence intensities and lifetimes of the solutions were compared.

Results

Clear differences can be seen between the two peptides. The intensity of the non-phosphorylated peptide was approximately 7×10$^4$ rfu, while that of the phosphorylated peptide was approximately 9×10$^4$ rfu. The lifetime of the non-phosphorylated peptide was about 10 nsec, whereas that of the phosphorylated peptide was 15 nsec. See FIG. 1.

Example 6

Assay of Tyrosine Kinase Abl

An Abl reaction mixture was prepared by mixing 1 ml of reaction buffer (50 mM Tris-HCl, 10 mM MgCl$_2$ 1 mM EGTA 2 mM dithiothreitol (pH 7.5 at 25° C.)), 10 µl of 10 mM ATP, 2 µl of 6-(9-oxo-9H-acridin-10yl) hexanoate-labelled Abl Peptide substrate (non-phosphorylated) (500 µM in DMSO). 100 µl of this mixture was placed into the wells of a black flat bottomed microtitre plate. The reaction was initiated by the addition of 10 µl of Abl kinase (New England Biolabs, Code P6050L Lot 5), (100,000 units/ml or 100 units/µl) which had been diluted in reaction buffer (50 mM Tris-HCl, 10 mM MgCl$_2$, 1 mM EGTA, 2 mM dithiothreitol, 0.01% Brij 35 (pH 7.5 at 25° C.) to a concentration of 100 units per 10 µl.

The reaction was monitored at 30 second intervals for both lifetime and intensity changes characteristic of the product and substrate.

Results

Figure 2:
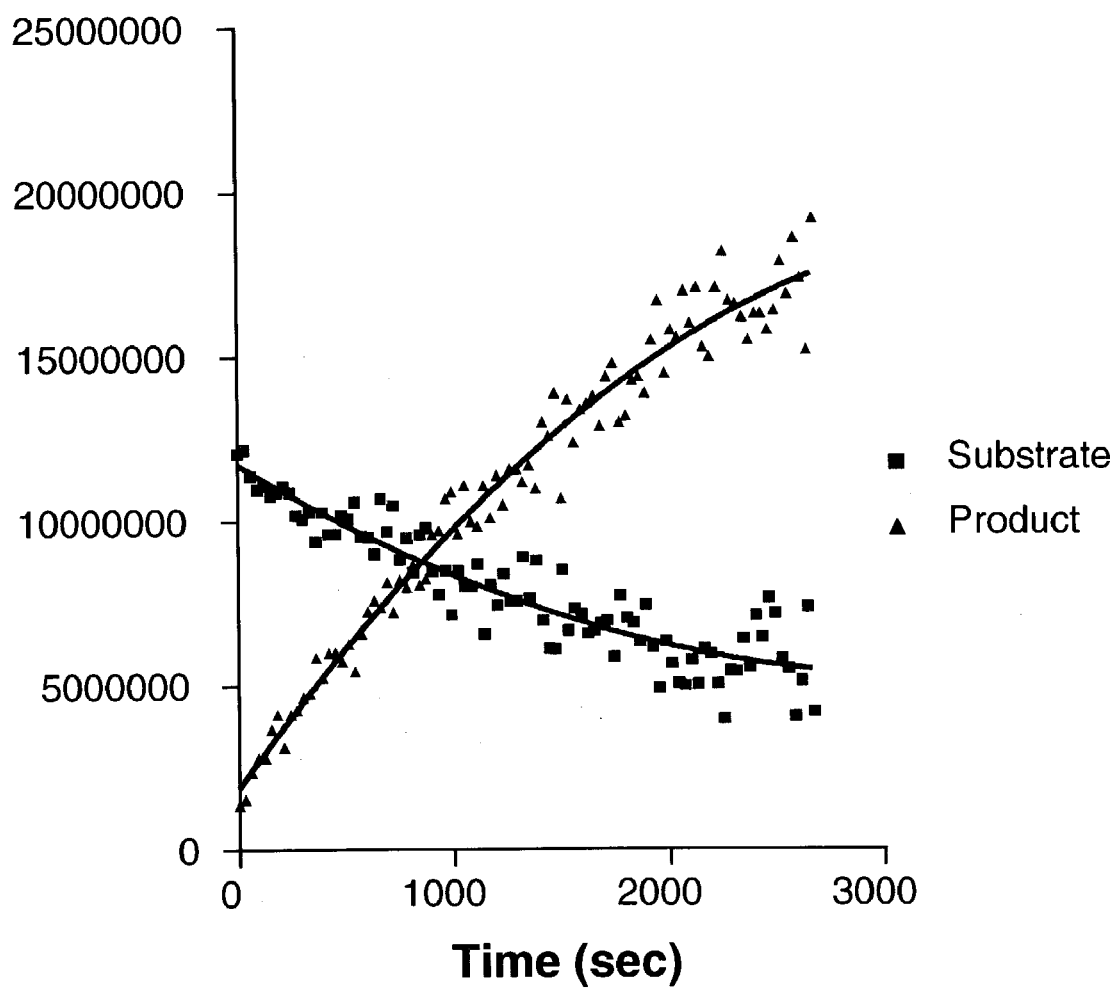
FIG. 2 illustrates the phosphorylation of a peptide by the protein tyrosine kinase Abl according to Example 6.

As shown in FIG. 2, the progress of the reaction may be monitored in real time. In particular, changes in the product intensity are greater than those of the substrate, as would be predicted from the study of the isolated peptides. Furthermore, it is possible to carry out this reaction with no separation step involved, and to distinguish the substrate and product on the basis of their respective fluorescent lifetimes.

Example 7

Time Dependent Phosphorylation of Myelin Basic Protein by Erk Kinase

Myelin Basic Protein (MBP) labelled with O-(N-succinimidyl)-6-(9-oxo-9H-acridin-10yl) hexanoate (prepared according to Example 2, Method 1) (1 ml) was diluted to 10 ml with water, giving a solution containing 50 mM MOPS, pH 7.2, 5 nM MgCl$_2$, 100 µM ATP and 1.66 µM MBP. Seven aliquots of 200 µl of reaction mixture were each mixed with 5 µl of Erk1 kinase (1.8 mg/ml). The reactions were incubated at room temperature for various times, 100 µl aliquots were withdrawn and the fluorescence of each aliquot was measured.

Results

Figure 3:
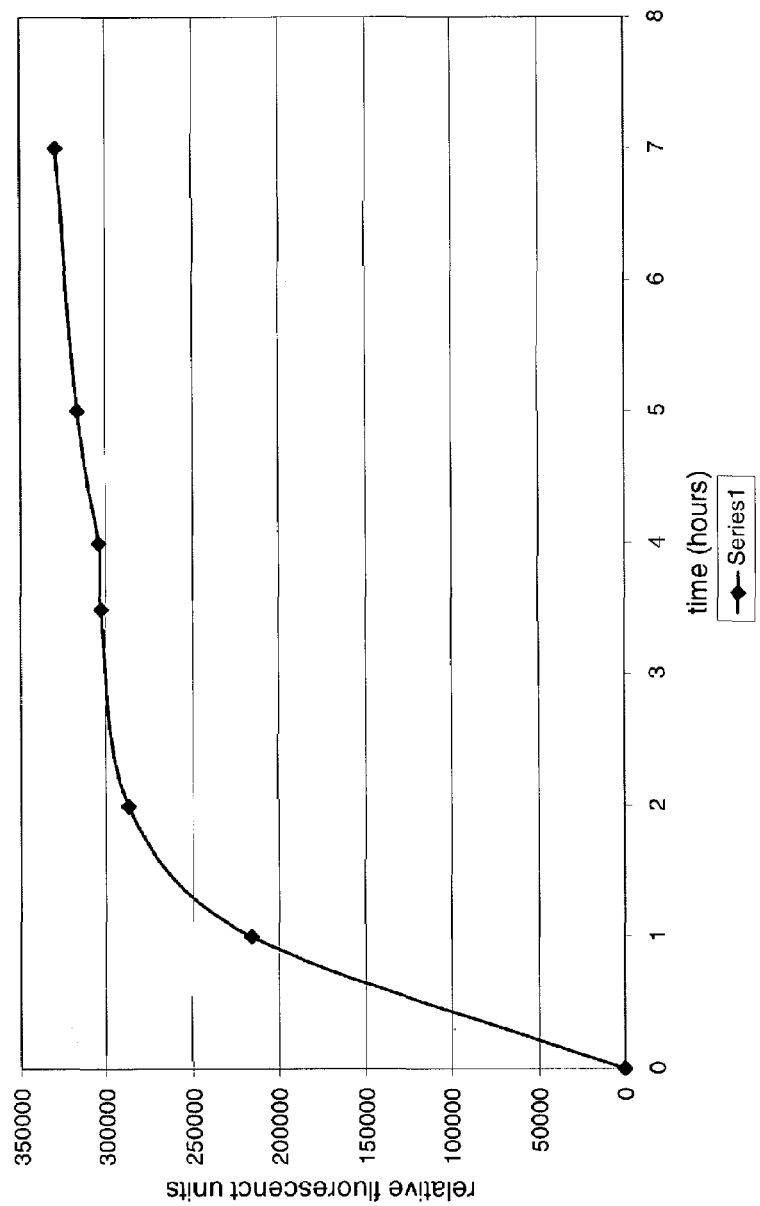
FIG. 3 is a plot showing the time dependent phosphorylation of Myelin Basic Protein by Erk kinase according to Example 7.

The results are shown in FIG. 3 and indicate a time-dependent increase in fluorescence.

Example 8

Inhibition of Erk kinase by Staurosporine

Myelin Basic Protein (MBP) labelled with O-(N-succinimidyl)-6-(9-oxo-9H-acridin-10yl) hexanoate (prepared according to Example 2, Method 1) (1 ml) was diluted to 10 ml with water, giving a solution containing 50 mM MOPS, pH 7.2, 5 nM MgCl$_2$, 100 µm ATP and 1.66 µM MBP. Seven 100 µl aliquots were made up to a concentration of 0–100 µM with respect to staurosporine. Finally, 2 µl of Erk 1 kinase (1.8 mg/ml) were added to each reaction mixture. The reaction mixtures were incubated at room temperature for 3 hours, after which time 100 µl of 100 mM EDTA were added to stop the reactions. Fluorescence intensities of the reactions were then determined.

Results

Figure 4:
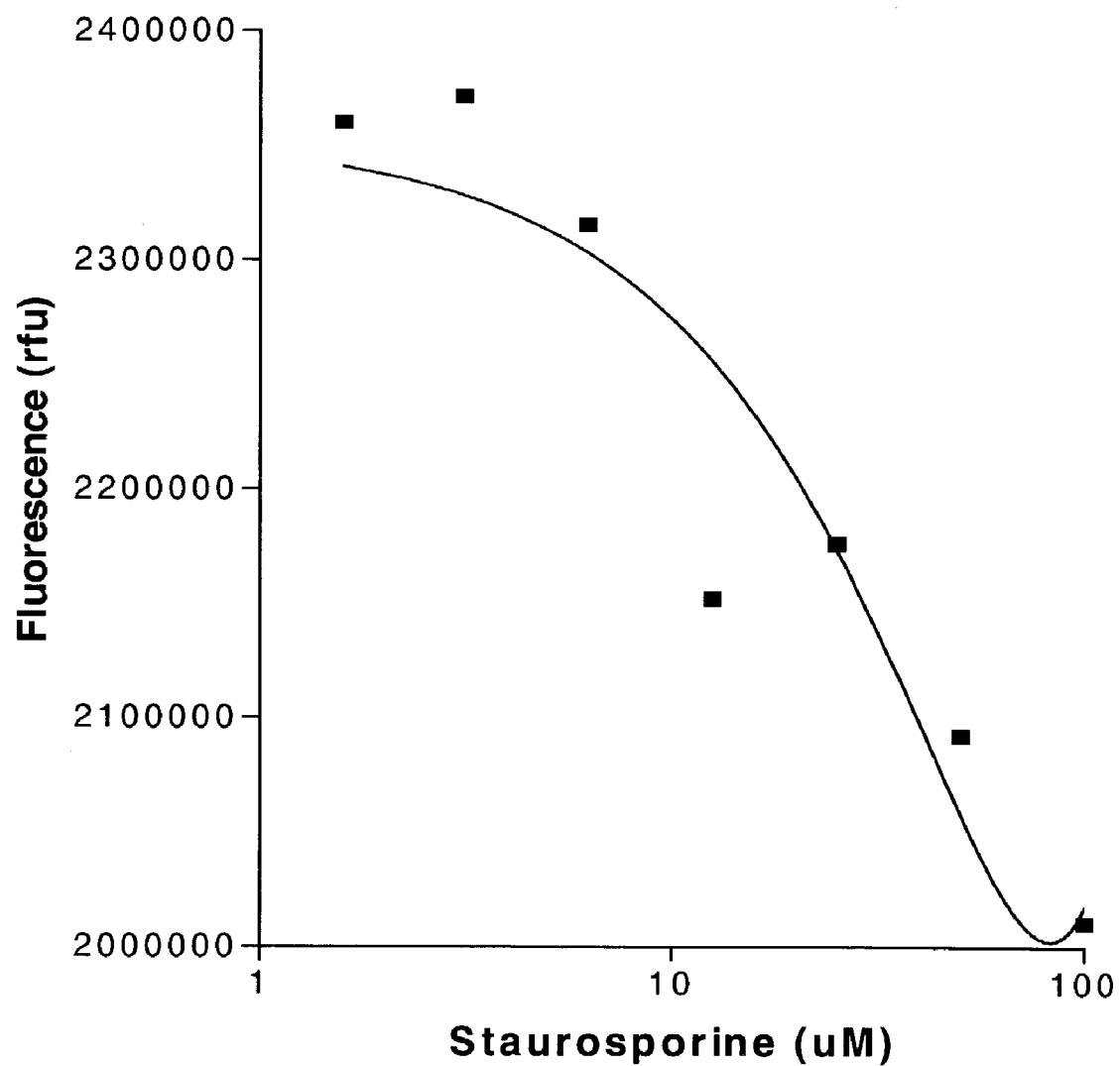
FIG. 4 is a plot showing inhibition of Erk kinase by staurosporine according to Example 8.

The enzyme reaction is inhibited in a dose dependent manner by staurosporine as shown in FIG. 4.

Example 9

Time-course for Phosphorylation by the Tyrosine Kinase Lck

Replicates of N-(6-(9-oxo-9H-acridin-10-yl)-hexanoyl)-Glu-Pro-Glu-Gly-Ile-Tyr-Gly-Val-Leu-Phe amide (500 nM) in 50 mM TRIS/10 mM $MgCl_2$/2.5 mM $MnCl_2$, pH 7.2 in the presence of 50 μM ATP in a volume of 100 μl were pipetted into the wells of a black 96-well microplate (Costar, Code 3650). The time-course was initiated by the addition of 12.7 milli-units of Lck enzyme (Upstate Biotechnology, Code 14-379) in a volume of 10 μl. The reaction was monitored at one minute intervals at ambient temperature for both lifetime and intensity changes characteristic of both substrate and product.

Results

Figure 5:
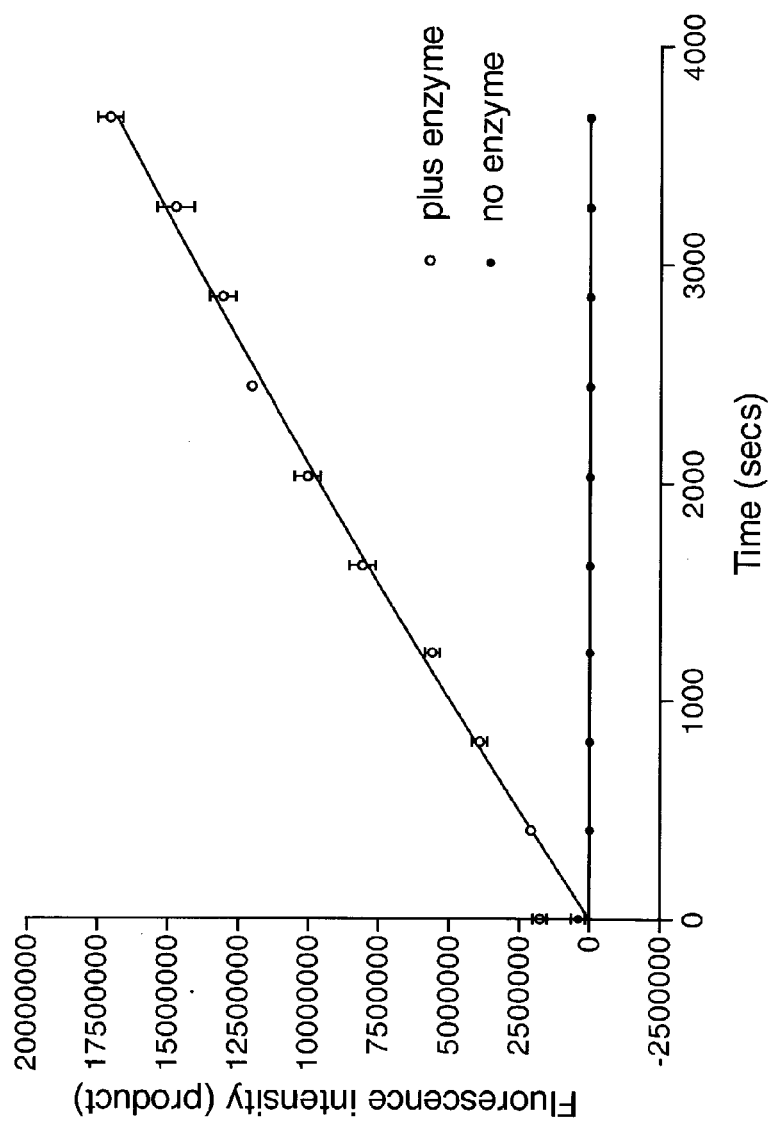
FIG. 5 is a time-course for phosphorylation by the tyrosine kinase Lck according to Example 9.

The results as shown in FIG. 5 indicate that the formation of product is dependent on time.

Example 10

ATP Dependence of Phosphorylation by the Tyrosine Kinase Lck

Replicates of N-(6-(2-acetamido-9-oxo-9H-acridin-10-yl)-hexanoyl)-Glu-Pro-Glu-Gly-Ile-Tyr-Gly-Val-Leu-Phe amide (500 nM) in 50 mM TRIS/10 mM $MgCl_2$/2.5mM $MnCl_2$, pH 7.2 and in the presence of various concentrations of ATP in a volume of 100 μl were pipetted into the wells of a black 96-well microplate (Costar, Code 3650). The reactions were initiated by the addition of 12.7 milli-units of Lck enzyme (Upstate Biotechnology, Code 14-379) in a volume of 10 μl. After incubation at room temperature for 60 minutes, the reactions were stopped by addition of 0.1M citrate buffer pH 3.0 (20 μl) to each well. The reactions was monitored for both lifetime and intensity changes characteristic of both substrate and product.

Results

Figure 6:
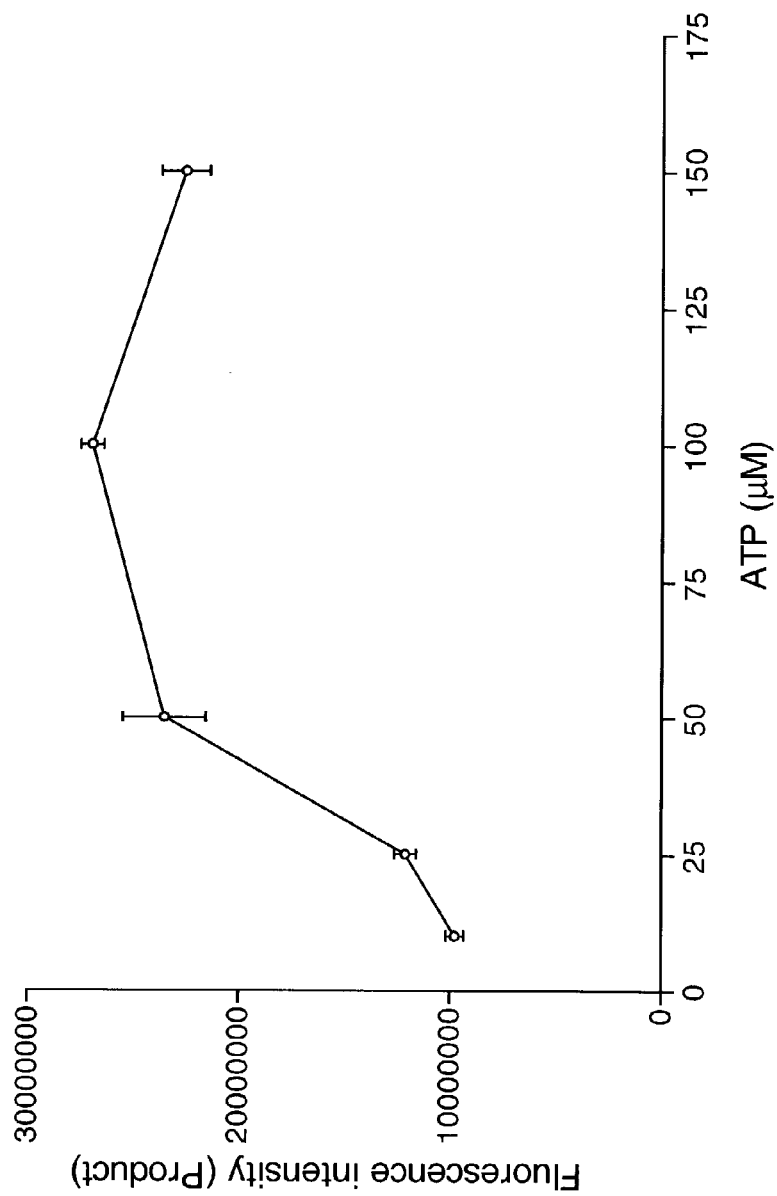
FIG. 6 is a plot illustrating ATP dependence of phosphorylation by the tyrosine kinase Lck according to Example 10.

The results are shown in FIG. 6, which indicates that the formation of product is dependent on the ATP concentration.

Example 11

Enzyme Dependence of Phosphorylation by the Tyrosine Kinase Lck

Replicates of N-(6-(9-oxo-9H-acridin-10-yl)-hexanoyl)-Glu-Pro-Glu-Gly-Ile-Tyr-Gly-Val-Leu-Phe amide (500 nM) in 50 mM TRIS/10 mM $MgCl_2$/2.5mM $MnCl_2$, pH 7.2 and presence of 50 μM ATP in a volume of 100 μl were pipetted into the wells of a black 96-well microplate (Costar, Code 3650). The reactions were initiated by the addition of quantities of Lck enzyme (Upstate Biotechnology, Code 14-379) in a volume of 10 μl. After incubation at room temperature for 90 minutes, the reactions were stopped by addition of 0.1M citrate buffer pH 3.0 (20 μl) to each well. The reactions was monitored for both lifetime and intensity changes characteristic of both substrate and product.

Results

Figure 7:
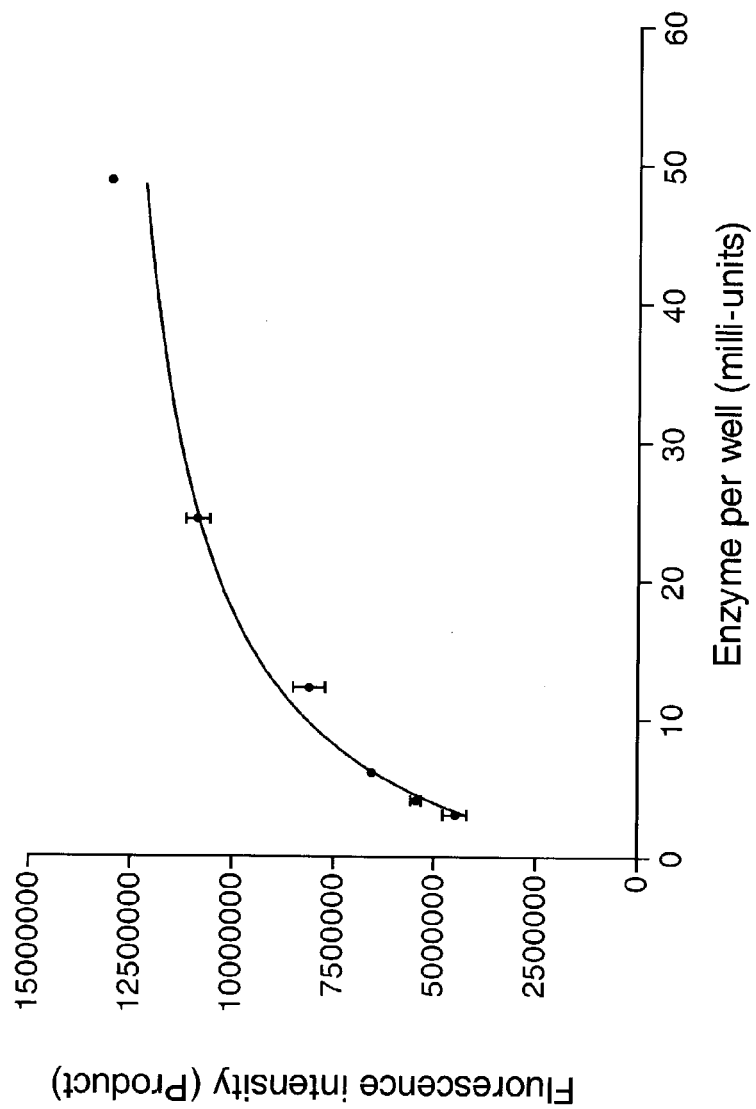
FIG. 7 is a plot showing enzyme dependence of phosphorylation by the tyrosine kinase Lck according to Example 11.

The results in FIG. 7 show that the formation of product is dependent on the enzyme concentration.

Example 12

Staurosporine Inhibition Curve with Tyrosine Kinase Lck

Staurosporine (Sigma, Code S4400, 1 mM in DMSO) was diluted with 10% (v/v) DMSO in assay buffer (50 mM TRIS/10 mM $MgCl_2$/2.5 mM $MnCl_2$, pH 7.2) to prepare the following concentrations of staurosporine—100 μM, 10 μM, 1 μM, 100 nM, 10 nM and 1 nM. Reaction mixture was prepared: 10 ml assay buffer+2.51 1 N-(6-(9-oxo-9H-acridin-10-yl)-hexanoyl)-Glu-Pro-Glu-Gly-Ile-Tyr-Gly-Val-Leu-Phe amide (1 mM)+20 μl ATP (10 mM). Five replicates (10 μl) of each inhibitor concentration were pipetted into the wells of a black 96-well microplate (Costar, Code 3650). Reaction mixture (100 μl) was added to each well. The reactions were initiated by the addition of 12.7 milli-units of Lck enzyme (Upstate Biotechnology, Code 14-379) in a volume of 10 μl. After incubation at room temperature for 60 minutes, the reactions were stopped by addition of 0.1M citrate buffer pH 3.0 (20 μl) to each well. The reactions were monitored for both lifetime and intensity changes characteristic of both substrate and product.

Results

Figure 8:
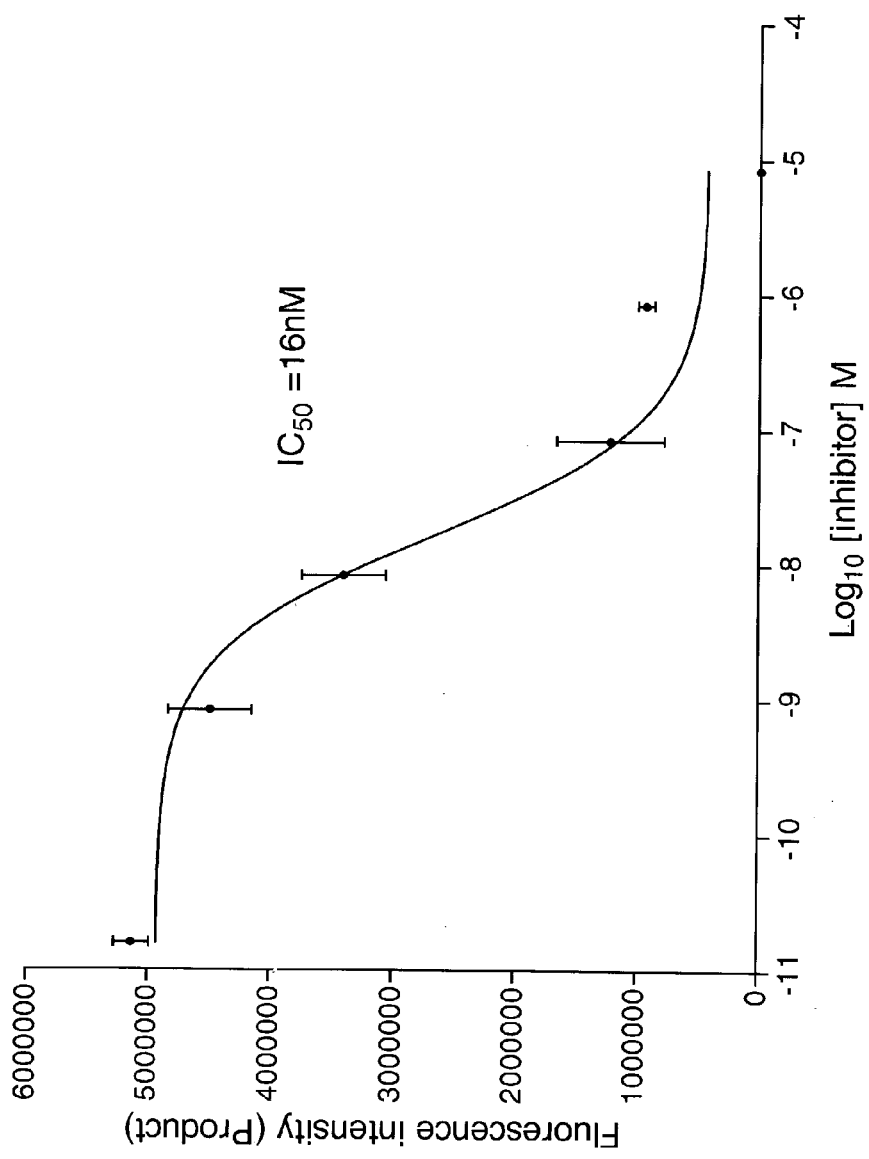
FIG. 8 is a plot showing inhibition of Lck kinase activity by staurosporine according to Example 12.

The results in FIG. 8 show the inhibition of Lck kinase activity by staurosporine; the $IC_{50}$ value is 16 nM. Park et al (Anal. Biochem., (1999), 269, 94–104) reported an $IC_{50}$ value of about 10 nM using ATP at 2 μM final concentration and a similar peptide sequence in a time-resolved fluorescence format assay.

Example 13

Time-course for Dephosphorylation Reaction by Protein-Tyrosine Phosphatase

Replicates of N-(6-(9-oxo-9H-acridin-10-yl)-hexanoyl)-Thr-Arg-Asp-Ile-Tyr($PO_3H_2$)-Glu-Thr-Asp-$NH_2$ (1 μM) in TRIS buffered saline, pH 7.6 in a volume of 100 μl were pipetted into the wells of a black 96-well microplate (Costar, Code 3650). The time-course was initiated by the addition of 88 units of protein-tyrosine phosphatase enzyme (Sigma, Code P9864) in a volume of 10 μl. The reaction was monitored at one minute intervals at ambient temperature for both lifetime and intensity changes characteristic of both substrate and product.

Results

Figure 9:
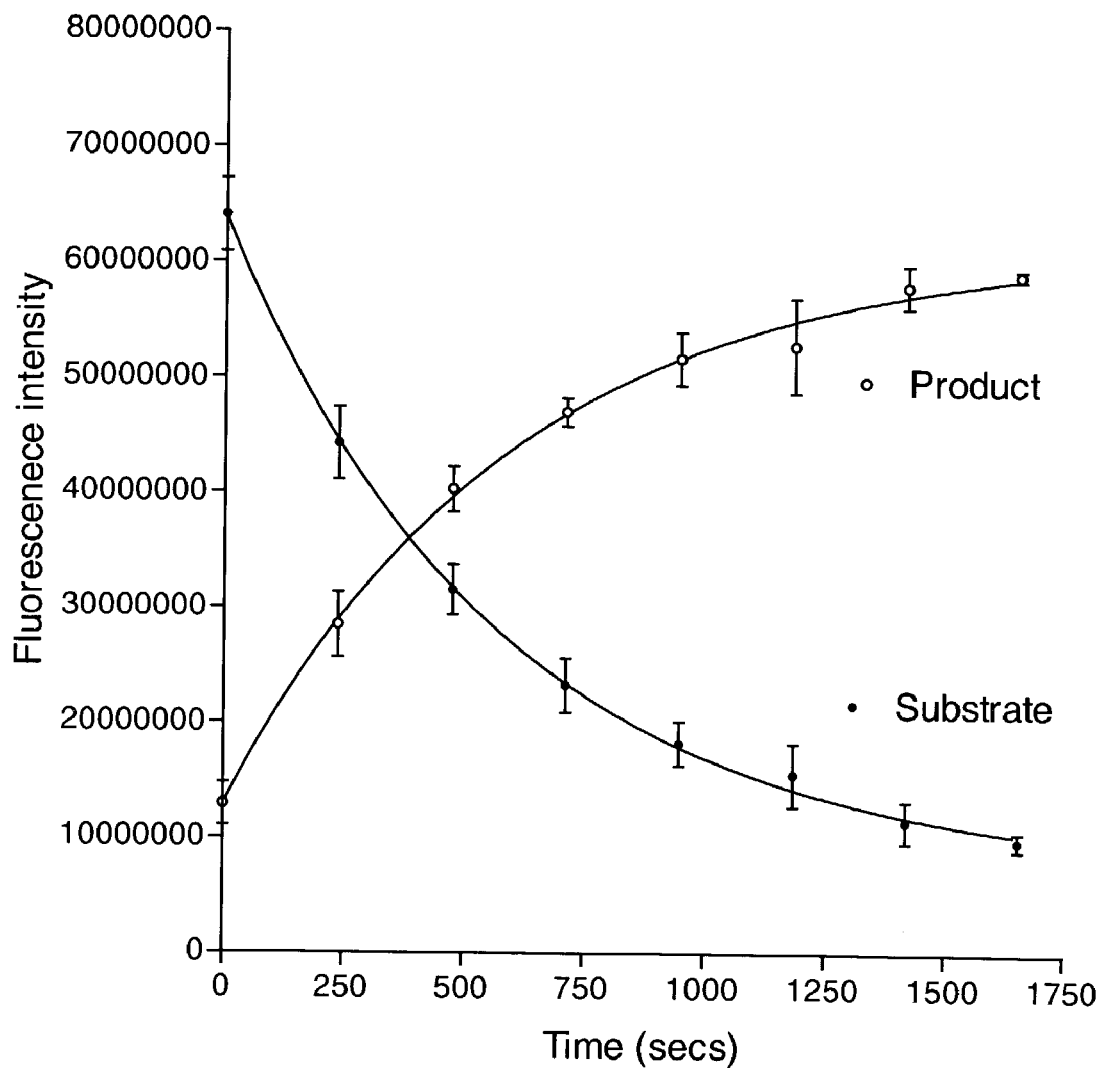
FIG. 9 is a time-course for a dephosphorylation reaction by protein-tyrosine phosphatase according to Example 13.

FIG. 9 is a plot showing the dephosphorylation of the substrate by this phosphatase. The appearance of the dephosphorylated product is also monitored.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A method for determining phosphorylating activity of an enzyme acting on a substrate molecule, said substrate comprising at least one moiety that is phosphorylated by said enzyme to yield a phosphorylated product and wherein said substrate is labelled with a fluorescent dye, said method comprising the steps of:
  i) measuring fluorescence intensity of the fluorescently labelled substrate;
  ii) combining said enzyme with said substrate molecule in the presence of a phosphate donor; and
  iii) measuring an increase in fluorescence intensity of the fluorescent label following step ii);
wherein said fluorescent dye is selected from the group consisting of acridone and quinacridone classes of dyes; and wherein said increase in fluorescence intensity of the fluorescent label is used to determine the phosphorylating activity of said enzyme.

2. The method of claim 1 wherein steps i) and iii) additionally comprise measuring fluorescence lifetimes of the fluorescent label; wherein an increase in fluorescence intensity and in fluorescence lifetime upon phosphorylation of the labeled substrate is used to determine the phosphorylating activity of said enzyme.

3. The method of claim 2 wherein the substrate is phosphorylated at a tyrosine residue by a tyrosine kinase, and wherein an increase in fluorescence lifetime is used to measure the concentration of phosphorylated product relative to the concentration of non-phosphorylated substrate.

4. The method of claim 1 wherein the substrate molecule is selected from the group consisting of natural proteins, post-translationally modified proteins, and synthetic peptides.

5. The method of claim 1 wherein the substrate molecule includes at least one amino acid that is phosphorylated.

6. The method of claim 5 wherein said amino acid is selected from the group consisting of tyrosine, serine, threonine and histidine.

7. The method of claim 1 wherein said substrate is phosphorylated by an enzyme selected from the group consisting of tyrosine kinase, serine/threonine kinase and histidine kinase.

8. The method of claim 1 wherein said phosphorylated product includes at least one phospho-tyrosine residue.

9. The method of claim 1 wherein said substrate is phosphorylated at a residue selected from the group consisting of serine, threonine and histidine.

10. The method of claim 1 wherein said substrate is labelled with a fluorescent dye of formula:

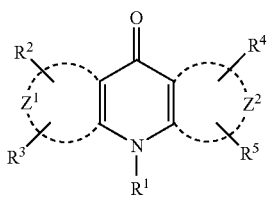

wherein:
  groups $R^2$ and $R^3$ are attached to the $Z^1$ ring structure and groups $R^4$ and $R^5$ are attached to the $Z^2$ ring structure;
  $Z^1$ and $Z^2$ independently represent the atoms necessary to complete one or two fused ring aromatic or heteroaromatic systems, each ring having five or six atoms selected from the group consisting of carbon atoms and optionally no more than two atoms selected from oxygen, nitrogen and sulphur;
  $R^1$, $R^2$, $R^3$, $R^4$ and $R^5$ are independently selected from the group consisting of hydrogen, halogen, amide, hydroxyl, cyano, amino, mono- or di-$C_1$-$C_4$ alkyl-substituted amino, sulphydryl, carbonyl, $C_1$-$C_6$ alkoxy, aryl, heteroaryl, $C_1$-$C_{20}$ alkyl, aralkyl, the group -E-F where E is a spacer group having a chain from 1–60 atoms selected from the group consisting of carbon, nitrogen, oxygen, sulphur and phosphorus atoms and F is a target bonding group, and the group —$(CH_2—)_nY$ where Y is selected from the group consisting of sulphonate, sulphate, phosphonate, phosphate, quaternary ammonium and carboxyl and n is zero or an integer from 1 to 6.

11. The method of claim 1 wherein said substrate is labelled with a fluorescent dye of formula:

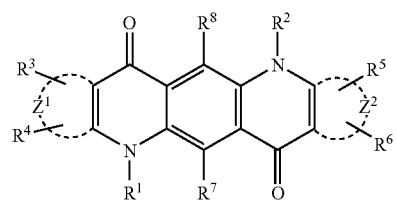

wherein:
  groups $R^3$ and $R^4$ are attached to the $Z^1$ ring structure and groups $R^5$ and $R^6$ are attached to the $Z^2$ ring structure;
  $Z^1$ and $Z^2$ independently represent the atoms necessary to complete one or two fused ring aromatic or heteroaromatic systems, each ring having five or six atoms selected from carbon atoms and optionally no more than two atoms selected from the group consisting of oxygen, nitrogen and sulphur;
  $R^1$, $R^2$, $R^3$, $R^4$, $R^5$, $R^6$, $R^7$ and $R^8$ are independently selected from the group consisting of hydrogen, halogen, amide, hydroxyl, cyano, amino, mono- or di-$C_1$-$C_4$ alkyl-substituted amino, sulphydryl, carbonyl, carboxyl, $C_1$-$C_6$ alkoxy, aryl, heteroaryl, $C_1$-$C_{20}$ alkyl, aralkyl, the group -E-F where E is a spacer group having a chain from 1–60 atoms selected from the group consisting of carbon, nitrogen, oxygen, sulphur and phosphorus atoms and F is a target bonding group, and the group —$(CH_2—)_nY$ where Y is selected from the group consisting of sulphonate, sulphate, phosphonate, phosphate, quaternary ammonium and carboxyl and n is zero or an integer from 1 to 6.

12. The method of claim 1 wherein said substrate is linked by a linker group to a solid support.

13. The method of claim 1 wherein said substrate is conjugated to a peptide or protein.

14. A method for determining dephosphorylating activity of an enzyme acting on a substrate molecule, said substrate comprising at least one phosphorylated moiety that is de-phosphorylated by said enzyme to yield a product and wherein said substrate is labelled with a fluorescent dye selected from the group consisting of acridone and quinacridone classes of dyes, said method comprising the steps of:
  i) measuring fluorescence intensity of the fluorescently labelled substrate;
  ii) combining said enzyme with said substrate molecule to yield a product; and
  iii) measuring a decrease in fluorescence intensity following step ii);
wherein said decrease in fluorescence intensity of the fluorescent label is used to determine the dephosphorylating activity of said enzyme.

15. The method of claim 14 wherein the substrate molecule is selected from the group consisting of natural proteins, post-translationally modified proteins, and synthetic peptides.

16. The method of claim 14 wherein the substrate molecule includes at least one phosphorylated amino acid that is dephosphorylated.

17. The method of claim 16 wherein said phosphorylated amino acid is selected from the group consisting of phosphorylated derivatives of tyrosine, serine, threonine and histidine.

18. The method of claim 14 wherein said enzyme removes a phosphate group from a phospho-tyrosine residue in said substrate and steps i) and iii) additionally comprise measuring the fluorescence lifetimes of the fluorescent label wherein a decrease in fluorescence lifetime is used to measure the concentration of phosphorylated substrate relative to the concentration of product.

19. The method of claim 14 wherein said substrate is labelled with a fluorescent dye of formula:

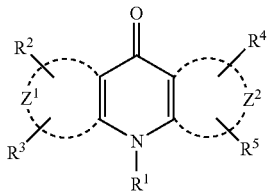

wherein:
groups $R^2$ and $R^3$ are attached to the $Z^1$ ring structure and groups $R^4$ and $R^5$ are attached to the $Z^2$ ring structure;

$Z^1$ and $Z^2$ independently represent the atoms necessary to complete one or two fused ring aromatic or heteroaromatic systems, each ring having five or six atoms selected from carbon atoms and optionally no more than two atoms selected from the group consisting of oxygen, nitrogen and sulphur;

$R^1$, $R^2$, $R^3$, $R^4$ and $R^5$ are independently selected from the group consisting of hydrogen, halogen, amide, hydroxyl, cyano, amino, mono- or di-$C_1$–$C_4$ alkyl-substituted amino, sulphydryl, carbonyl, $C_1$–$C_6$ alkoxy, aryl, heteroaryl, $C_1$–$C_{20}$ alkyl, aralkyl, the group -E-F where E is a spacer group having a chain from 1–60 atoms selected from the group consisting of carbon, nitrogen, oxygen, sulphur and phosphorus atoms and F is a target bonding group, and the group —$(CH_2—)_n$Y where Y is selected from the group consisting of sulphonate, sulphate, phosphonate, phosphate, quaternary ammonium and carboxyl and n is zero or an integer from 1 to 6.

20. The method of claim 14 wherein said substrate is labelled with a fluorescent dye of formula:

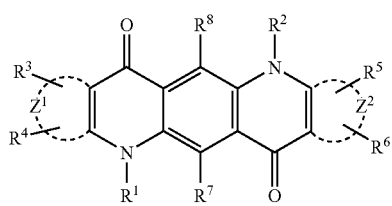

wherein:
groups $R^3$ and $R^4$ are attached to the $Z^1$ ring structure and groups $R^5$ and $R^6$ are attached to the $Z^2$ ring structure;

$Z^1$ and $Z^2$ independently represent the atoms necessary to complete one or two fused ring aromatic or heteroaromatic systems, each ring having five or six atoms selected from carbon atoms and optionally no more than two atoms selected from the group consisting of oxygen, nitrogen and sulphur;

$R^1$, $R^2$, $R^3$, $R^4$, $R^5$, $R^6$, $R^7$ and $R^8$ are independently selected from the group consisting of hydrogen, halogen, amide, hydroxyl, cyano, amino, mono- or di-$C_1$–$C_4$ alkyl-substituted amino, sulphydryl, carbonyl, carboxyl, $C_1$–$C_6$ alkoxy, aryl, heteroaryl, $C_1$–$C_{20}$ alkyl, aralkyl, the group -E-F where E is a spacer group having a chain from 1–60 atoms selected from the group consisting of carbon, nitrogen, oxygen, sulphur and phosphorus atoms and F is a target bonding group, and the group —$(CH_2—)_n$Y where Y is selected from the group consisting of sulphonate, sulphate, phosphonate, phosphate, quaternary ammonium and carboxyl and n is zero or an integer from 1 to 6.

21. The method of claim 14 wherein said substrate is linked by a linker group to a solid support.

22. The method of claim 14 wherein said substrate is fused to a peptide or protein.

23. The method of claim 14, wherein steps i) and iii) additionally comprise measuring fluorescence lifetimes of the fluorescent label; wherein a decrease fluorescence intensity and in fluorescence lifetime upon dephosphorylating the labeled substrate is used to determine the dephosphorylating activity of said enzyme.

24. A method of simultaneously measuring kinase activities of two or more different enzymes each enzyme specific for a different substrate, wherein each substrate comprises at least one moiety that phosphorylated by an enzyme to yield a product, and wherein each said substrate is labelled with a different one of a set of fluorescent dyes, said method comprising the steps of:
i) measuring fluorescence intensity and fluorescence lifetime of each of the fluorescently labelled substrates;
ii) combining a mixture of said enzymes with each of said substrates in the presence of a phosphate source; and
iii) measuring an increase in fluorescence intensity and in fluorescence lifetime of each of the fluorescent labels following step ii);
wherein the fluorescent dyes in said set are selected from the group consisting of acridone and guinacridone classes of dyes; and wherein said increase in fluorescence intensity and in fluorescence lifetime of each of the fluorescent labels is used to determine the phosphorylating activity of each of said enzymes.

25. The method of claim 24 wherein said enzymes are isolated enzymes.

26. The method of claim 24 wherein one or more of said enzymes is a component of a cell lysate.

27. The method of claim 24 wherein step ii) is performed in a cellular environment and wherein each of the different substrates is conjugated to a carrier or transport peptide.

28. The method of claim 24 wherein the kinase activities that are measured are tyrosine kinases.

* * * * *